(12) United States Patent
De Bruijn et al.

(10) Patent No.: US 8,934,005 B2
(45) Date of Patent: Jan. 13, 2015

(54) SYSTEM AND METHOD FOR REMOTE MEASUREMENT OF OPTICAL FOCUS

(75) Inventors: Frederik Jan De Bruijn, Eindhoven (NL); Ruud Vlutters, Eindhoven (NL); Harold Agnes Wilhelmus Schmeitz, Eindhoven (NL); Tommaso Gritti, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 0 days.

(21) Appl. No.: 14/232,016

(22) PCT Filed: Jul. 3, 2012

(86) PCT No.: PCT/IB2012/053369
§ 371 (c)(1),
(2), (4) Date: Jan. 10, 2014

(87) PCT Pub. No.: WO2013/008129
PCT Pub. Date: Jan. 17, 2013

(65) Prior Publication Data
US 2014/0168401 A1    Jun. 19, 2014

Related U.S. Application Data

(60) Provisional application No. 61/507,676, filed on Jul. 14, 2011.

(51) Int. Cl.
*H04N 7/18* (2006.01)
*G06F 3/01* (2006.01)
*A61B 3/10* (2006.01)

(52) U.S. Cl.
CPC .................. *H04N 7/18* (2013.01); *G06F 3/013* (2013.01); *A61B 3/10* (2013.01)
USPC ........................................................... 348/78

(58) Field of Classification Search
CPC ............. H04N 7/18; G06F 3/013; A61B 3/10
USPC .......................................................... 348/78
See application file for complete search history.

(56) References Cited

U.S. PATENT DOCUMENTS

| 3,524,702 A | 8/1970 | Bellow et al. |
| 3,639,041 A | 2/1972 | Cornsweet |
| 5,523,809 A | 6/1996 | Kohayakawa |

FOREIGN PATENT DOCUMENTS

| DE | 1136847 B | 9/1962 |
| DE | 1299907 B | 7/1969 |

OTHER PUBLICATIONS

Sheimpflug Principle, Wikipedia Summary of a Geometric Rule on the Plane of Focus of an Optical System, Downloaded From "http://en.widipedia.org/wiki/Scheimpflug_principle_" on Dec. 23, 2010, 10 Page Document.

(Continued)

*Primary Examiner* — Allen Wong

(57) ABSTRACT

A system and method that measures an optical focus of a distant optical imaging system (EYE), in particular the ocular accommodation of a distant human subject. A luminous pattern of light (P1, A1) is projected by a projector (P) in focus (A2) at a known focal plane (FPL1) in front of the distant optical imaging system (EYE), and an image of the reflection of the pattern (A3) on a sensor surface of the distant optical imaging system (EYE), for instance the retina of an eye, is recorded by a camera (CAM) having an optical axis (AXCAM) coinciding at least partly with or situated close to the optical axis (AXP) of the projection device (P). The sharpness of the luminous pattern (A3) reflected from the sensor surface (retina) is determined.

18 Claims, 10 Drawing Sheets

(56) References Cited

OTHER PUBLICATIONS

Shack-Hartmann, Wikipedia Summary of a Wavefront Sensor, Downloaded From "http://en.wikpedia.org/wiki/Shack-Harmann", on Nov. 1, 2010, 2 Page Document.
Mohan et al: Bokode:Imperceptible Visual Tags for Camera Based Interaction From a Distance; Abstract, ACM Transactions on Graphics (Proceedings of SIGGRAPH 2009), pp. 1-8.
Pamplona et al: "Netra:Interactive Display for Estimating Refractive Errors and Focal Range"; ACM SIGGRAPH 2010, Transactions on Graphics, vol. 29(4), 2010, pp. 1-8.
Hecht: "Optics", Addison Wesley Publishers, 2002, Chapter 4, "The Propagation of Light"; 4.5 Fermat's Principle, pp. 106-107.
Trusit Dave: "Automated Refraction, Design and Applications"; 2004 OT, pp. 28.
Zhu et al: "Microfluctuations of Wavefront Abberations of the Eye"; Ophthal. Physiol. Opt. 2004, Issue 24, pp. 562-571.
Campbell et al: "High-Speed Infrared Optometer"; Journal of the Optical Society of America, vol. 49, No. 3, Mar. 1959, pp. 268-272.
Biedermann: "The Eye, Harmann, Shack, and Scheiner"; Society of Photo-Optical Instrumentation Engineers, 2002, pp. 123-130.
Takeda et al: "Three-Dimensional Optometer III"; Applied Optics, vol. 32, No. 22, Aug. 1993, pp. 4155-4168.
Van Der Heijde et al: "Microfluctuations of Steady-State Accommodation Measured With Ultrasonography"; Ophthal Physio. Opt., vol. 16, No. 3, 1996, pp. 216-221.
Warshawsky: "High-Resolution Optometer for the Continuous Measurement of Accommodation"; Journal of the Optical Society of America, vol. 3, Mar. 1964, pp. 375.
Okuyama et al: "Eye-Tracking Infra-Red Optometer"; Ophthal. Physiol. Opt., vol. 10, Jul. 1990, pp. 291-299.
Heron et al: "Accommodation Responses and Ageing"; Investigative Ophthalmology & Visual Science, Nov. 1999, vol. 40, No. 12, pp. 2872-2882.
Okuyama et al: "Binocular Infrared Optometer for Measuring Accommodation in Both Eyes Simultaneously in Natural-Viewing Conditions"; Applied Optics, Aug. 1993, vol. 32, No. 22, pp. 4147-4154.
Taylor: "The Automatic Eye Alignment of an Infrared Optometer": Thesis Sumitted to AUT University, 2009 128 Pages.
Winn et al: "Current Perpective on Microfluctuations"; Ophthal. Physiol. Opt., 1992, vol. Apr. 1992, pp. 252-256.
Cossairt et al: "Diffusion Coded Photography for Extended Depth of Field"; SIGGRAPH 2010, vol. 29, Issue 4, Jul. 2010, pp. 1-10.

(a)

(b)

(c)

SYSTEM AND METHOD FOR REMOTE MEASUREMENT OF OPTICAL FOCUS

CROSS-REFERENCE TO PRIOR APPLICATIONS

This application is the U.S. National Phase application under 35 U.S.C. §371 of International Application No. PCT/IB2012/053369, filed on Jul. 3, 2012, which claims the benefit of U.S. Provisional Patent Application No. 61/507,676, filed on Jul. 14, 2011. These application are incorporated by reference herein.

FIELD OF THE INVENTION

The invention relates to a measurement system for remote measurement of an optical focus of a distant optical imaging system, the distant optical imaging system comprising a lens and a sensor surface, wherein the measurement system comprises a means for providing a luminous pattern, a device for recording an image of the optical imaging system, and a means for determining from the image of a reflection of the luminous pattern on the sensor surface the optical focus of the distant optical imaging system.

The invention further relates to a method for remotely measuring optical focus of a distant optical imaging system, the distant optical imaging system comprising a lens and a sensor surface, wherein a luminous pattern is provided and wherein an image of a lens of the optical imaging system is recorded, and wherein from the image of a reflection of the luminous pattern on the sensor surface the optical focus of the distant imaging system.

BACKGROUND OF THE INVENTION

Measurement systems and methods as described above exist and they are in particularly used for remote measurement of ocular accommodation of a distant (human) eye.

In clinical practice, the objective measurement of ocular accommodation is necessary for patients who are unable to undergo a subjective refraction test that requires a judgment and response from the individual (such as very young infants). The aim is then to measure the refractive condition (typically near- or farsightedness) of the eye to determine the strength of the prescription glasses. In addition to clinical applications, also in human vision research, continuous measurement of accommodation is used to obtain insight in the physiology and the dynamic behaviour of the eye.

The oldest way to measure the refractive condition in an objective way was by direct observation of the projection of a moving light source on the retina, known as retinoscopy. The retinal projection of the light source causes a retroreflection on the retina of which the movement is indicative for the refractive condition.

As early as 1619, a method was introduced by Scheiner, replacing the moving light by an illumination through a punctured plate, which is placed close to the eye. The holes in the plate essentially create luminous pattern comprising a discrete set of light rays which are to converge on a single point on the retina, i.e. the sensor surface of the eye, in case of proper accommodation. The appearance of multiple retinal projections is again an indication for near- or farsightedness. The Scheiner principle still forms the basis for modern automatic refractometers, or autorefractors.

Warshawsky uses the Scheiner principle to build a mechanical autorefractor as described in "High-resolution optometer for the continuous measurement of accommodation", Journal of the Optical Society of America, vol 54, nr. 3 pp 375-379, March 1964. Similar methods and systems are described in Campbell et al in "High-speed infrared optometer" Journal of the Optical Society of America, vol 49, nr. 3, March 1959 and Okayama et al in "Eye-tracking infrared optometer", Ophthalmic and Physiological Optics, Vol. 10, July 1990.

Most of the modern autorefractors continue to be based on the Scheiner principle. All known devices, however, have the disadvantage that the systems and methods are obtrusive. Many systems and methods require the user to look straight into the measuring device, which is quite obtrusive and does not mimic a natural behaviour. For instance, although the autorefractor by Okuyama provides a view on natural targets, the obstruction by the semitransparent mirrors in the vicinity of the eyes and the need for a chin-rest do not create a natural viewing experience.

It is well known that many people when put in an unnatural position and clearly put under observation feel uncomfortable and this may affect such phenomena as heart rate and blood pressure which may have an effect on vision. Apart from the obvious disadvantage of possibly placing the observed object under stress, there is also the disadvantage of obtaining results which do not actually reflect the eye accommodation in normal situations, but the eye accommodation when the subject is put under stress.

SUMMARY OF THE INVENTION

It is an object of the invention to provide a method and system of the type as described in the opening paragraphs for remotely and unobtrusively measuring the ocular accommodation.

To that end, the system of the invention is a system comprising a light projection device for projecting the luminous pattern of light such that the pattern is in focus at a known focal plane in front of the lens of the distant optical imaging system, and a camera having an optical axis coinciding at least partly with or situated close to the optical axis of the projection device for recording an image of the reflection of the pattern on the sensor surface of the distant optical imaging system and a means for determining the sharpness of the luminous pattern reflected on the sensor surface.

The method and system of the invention is based on the use of a projection device generating visible or invisible (e.g. infrared) light, and one or more cameras of which the optical axis is at least at the optical plane of the projection device oriented along or close to the axis of the projection device. When the focus plane of projector and camera coincide with the focus plane of the distant optical imaging system positioned beyond, as seen from the projection device, the focal plane of the projector, the projected pattern appears sharp on the camera, i.e. the recording device of the measurement system. A single pattern can be used. Image processing is preferably used to enhance and analyse the captured images preferably as part of an automated system.

In preferred embodiments the projection device is arranged to generate more than one pattern at different focal planes. The use of different patterns projected at different distances, which forms a preferred embodiment, allows instant detection of multiple focus distances, based on whichever pattern appears sharp.

The system comprises in preferred embodiments a common lens for projection device and camera. This reduces the complexity of the measurement system.

Wherein, in the present invention the word "camera" is used, any imaging device is captured under the word "camera".

Light to make the pattern may be visible light, but is preferably IR light so as not to disturb the viewer.

So as not to disturb, and yet use patterns in visible light, the visible light patterns is hidden in the projected light in preferred embodiments.

In many circumstances the distant optical imaging system will be an eye of a human and the system and method of the invention is particularly useful for such applications; however, it may also be the eye of an animal such as a cat, dog or horse of even the lens of a camera. The advantage of remote measurement of accommodation allows measurement of ocular accommodation with animals, which is impossible, if not very difficult, with known methods and systems. It may also be used to track the operation of a camera. The measurement system can be part of an attentive user interface, a safety monitoring system or a surveillance system.

The method of the invention is characterized in that the luminous pattern of light is projected in focus at a known focal plane in front of the lens of the distant optical imaging system, and an image of the reflection of the pattern on the sensor surface of the distant optical imaging system is recorded by a camera having an optical axis coinciding at least partly with or situated close to the optical axis of the projection device and the sharpness of the luminous pattern reflected on the sensor surface is determined.

BRIEF DESCRIPTION OF THE DRAWINGS

These and other objects and advantageous aspects will become apparent from exemplary embodiments that will be described using the following Figs.

The figures are not drawn to scale. Generally, identical components are denoted by the same reference numerals in the figures.

DETAILED DESCRIPTION OF PREFERRED EMBODIMENTS

Figure 1:
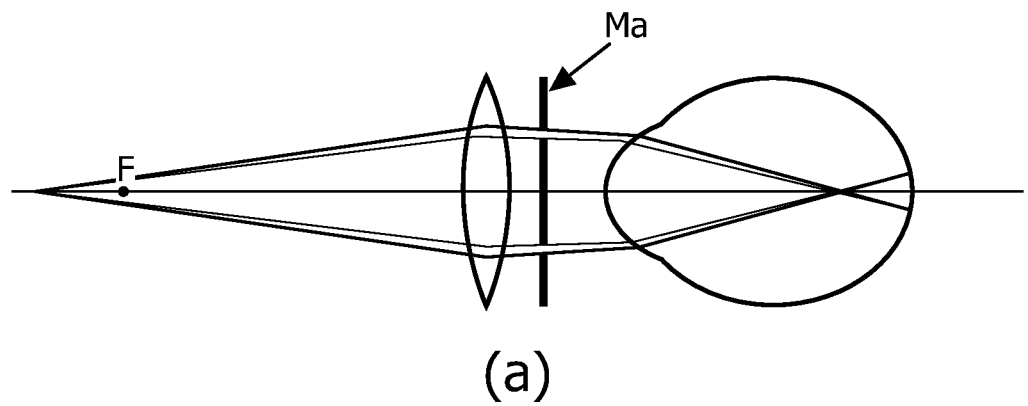
FIG. 1 illustrates the Scheiner principle, which is the principle of all known refractometers.
Figure 1:
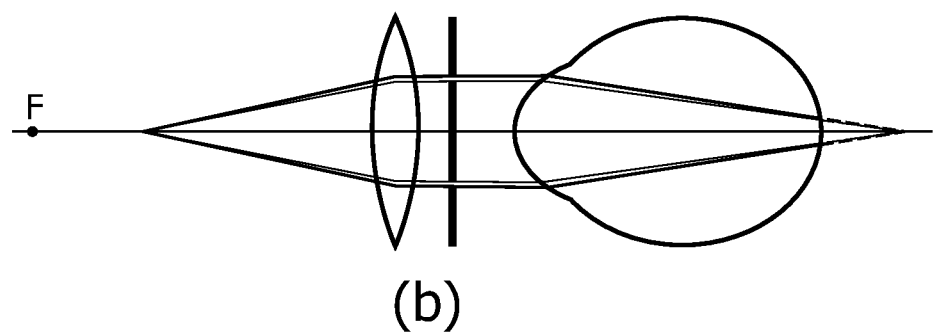
Figure 1:
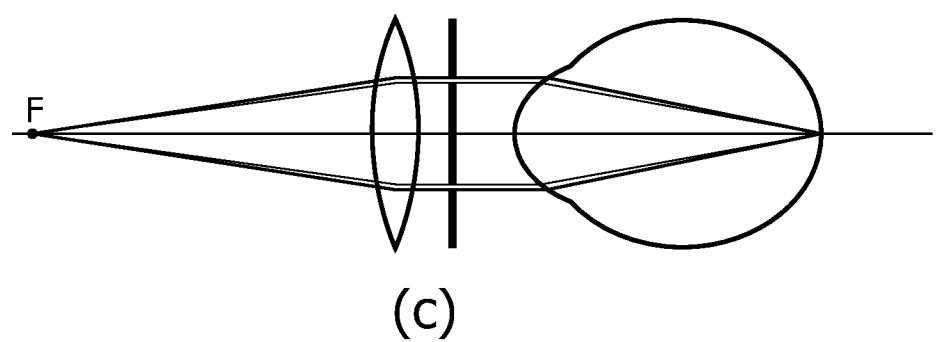

FIG. 1 illustrates the Scheiner principle, which is the principle of all known refractometers.

An external lens with focal point F is placed in front of a mask Ma with a double pinhole. Only in the case of correct accommodation, both spots merge on the retina to constitute one single, brighter spot (indicated at (c)).

Figure 2:
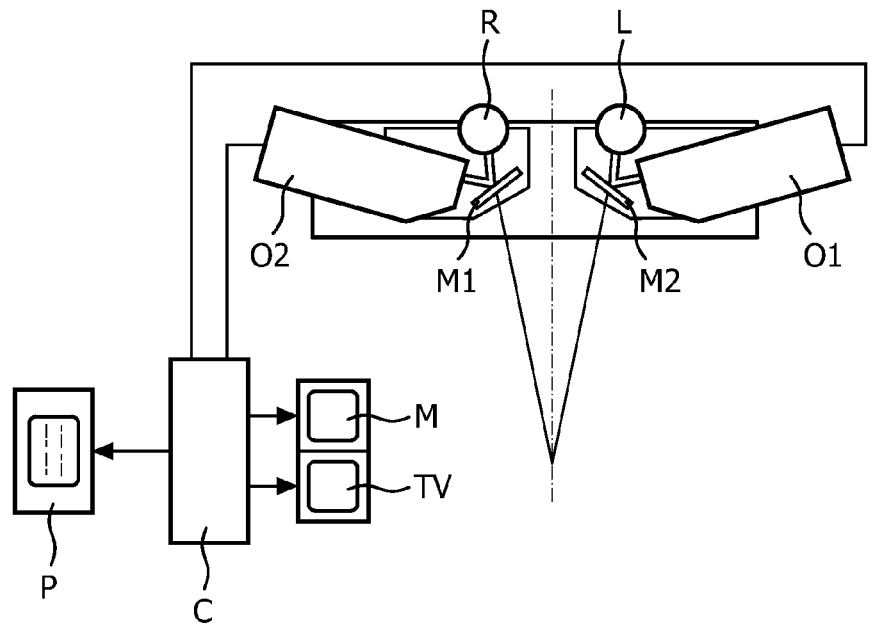
FIG. 2 illustrates a known set-up.

FIG. 2 illustrates an optometer as proposed by Okuyama.

Dichoric mirrors M1 and M2 are positioned before the left L and right R eye, left and right optometers O1 and O2 are used. The signals are sent to a control unit C which may send the outcome to a pen recorder P, a monitor M and/or a TV.

Clearly, although the autorefractor by Okuyama provides a view on natural targets, the obstruction by the semitransparent mirrors in the vicinity of the eyes and the need for a chin-rest do not create a natural viewing experience.

The invention has as an object to provide the possibility to remotely detect the focusing distance of lens-based imaging systems from a large distance.

To this end, the system of the invention comprises a light projection device for projecting one or more patterns of light and means for providing the one or more patterns at one or more known focal planes, and a camera having an optical axis coinciding at least for a part with the optical axis of the projection device for measuring an image of reflection of the one or more light patterns on an image plane of the lens and an image processor for analyzing the sharpness of the one or more reflected pattern.

As the invention also works for (human) eyes, it provides the focus distance to which accommodation takes place, thus revealing the distance to the momentary object of attention.

In contrast to existing systems for measuring ocular accommodation, the invention is totally unobtrusive, such that accommodation is measured without having to obstruct the view by semitransparent optics in the viewing path or elements in the periphery of the eye.

In contrast to existing systems for measuring ocular accommodation, the proposed system can be constructed with a small form factor, typically having the size of a pico-beamer or a webcam.

The simple construction of the optics and the potentially simple detection of proper focus enable a low-cost implementation.

The use of patterns, known by the image processing-unit, makes the focus detection is inherently robust to motion, as the particular pattern in focus will always be relayed back by the eye to more or less the same location in the frame of the coaxial camera. This is simply due to the coaxial geometry. This makes the system robust to motion blur as well.

Use of multiple patterns, as described in the embodiments, should also allow simultaneous detection of the individual ocular accommodation of multiple human subjects.

Figure 3:
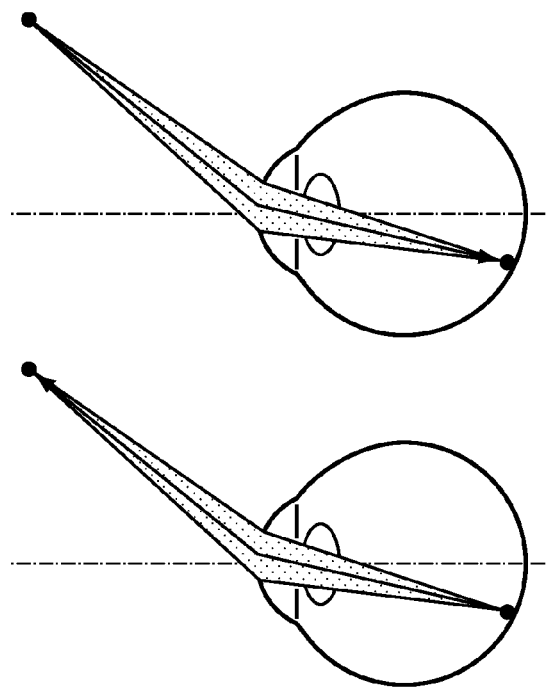
FIG. 3 illustrates the capture of autoreflection or retroreflection.

FIG. 3 illustrates the principle of retro-reflection. The red-eye effect, i.e. the retinal reflection, is relatively independent of the gaze direction; the subject need not be looking in the direction of the camera or the adjacent flashlight. A light source creates a bright retinal projection. As the subject tends to focus on the camera and flashlight, the light efficiently concentrates on the retina, causing the spot of the light source on the retina to function as a secondary light source projecting from the eye outward to the source of light. Based on Fermat's principle the conjugate points of the light source and the image of the light source on the retina image fall on each other, regardless the direction of the light, such that the image of the reflection of the light source on the retina and the light source are at the same point. As a consequence, the eye has a natural retroreflecting property.

Figure 4:
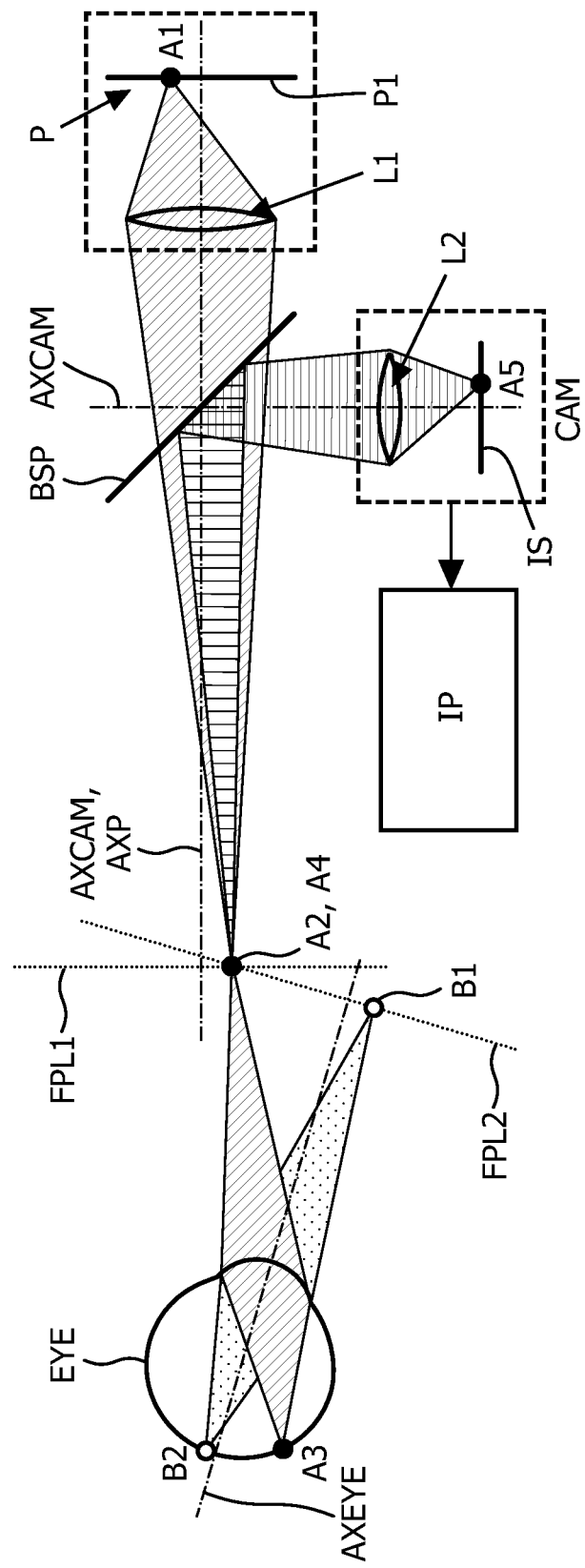
FIG. 4 illustrates a system and method of the invention.

FIG. 4 illustrates the system and method of the invention.

The projector P and camera CAM share the same optical axis, i.e. AXCAM and AXP coincide, by the use of a beam splitter BSP, which can be a semitransparent mirror. The projector projects a pattern such that each point A1 of pattern P1 is projected at point A2 such that the collection of points of the pattern forms a sharp image of that pattern at the focal plane FPL1. The projector and camera are provided with lenses L1 and L2 respectively.

If we would place a screen at the focal plane of the projector, the camera would be able to capture the projection A2, which would only appear as a single point A5 on the sensor if its focus plane coincides with that of the projector. However, there is no screen. In absence of a physical projection screen, the remote imaging system, in this case the eye EYE will focus point A2 on the retina at point A3 and will relay via point A4 the point back into the camera on point A5, under the condition that point A2 happens to be situated in the focal plane of the remote imaging system, in this case the eye, i.e. on focal plane FPL2. In FIG. 4, the remote eye is focused on point in space B2, which is therefore positioned in the momentary focal plane FPL2 of the eye (note that the real focal plane of the eye will be a focal surface with a certain curvature). In doing so, the eye's focal plane coincides with the focal plane FPL1 of camera and projector. As a consequence, it is forming a sharp image on the eye's retina. In practice, the entire projected pattern will be relayed back in focus as the depth of field of each of the three imaging systems tends to spread the area of coincident focus into a 3D volume around the two focal planes. Of course, the volume of coincident focus decreases when the angle between the two optical axes becomes larger.

The focus detection is based on the fact that the projected pattern, or at least an aspect of the projected pattern (such as orientation), is known by the image processing unit. In order to detect the occurrence of the focus at a predetermined plane, the remote imaging system, the eye, will relay a fragment of the pattern back to the camera as if only that fragment would be projected on a physical screen at the same distance. To put it simply, only if the focal planes of the eye and the focal plane of the projector and camera coincide, the camera will record a sharp retroreflection of the pattern on the retina. FIG. 4 shows that nothing is in between the eye EYE and the focal plane of the eye FPL2. The ocular accommodation measurement is done from a distance. The person under investigation does not have to look into the measuring device or have a semitransparent mirror positioned in front of the eyes, nor have to use a chin-rest. The method is totally unobtrusive and, if IR light is used can even be used without the person being aware of observation. Examples of using visible light which would nevertheless not be perceived or at least not distractive for a viewer are given below. In this example the eye is focusing in point B1; the image of B1 is at point B2 on the retina, the retina being the sensor surface of the distant optical imaging system, being a human eye.

The new principle of focus detection on the basis of a common focus plane can be used for focus estimation or focus measurement or focus tracking within a predetermined range of focus distances. Using the detection of focus as a basis, there are various methods for estimation or measurement of focus from a range of focus distances.

Using a single projected luminous pattern, an embodiment of the invention is based on the combined adjustment of the common focus distances of projector and camera. Using the new focus detection principle, the common focus plane of projector and camera is adjusted until the project pattern is optimally detected from the eye, i.e. the reflection of the pattern on the retina is sharpest. The so found value of the common focus distance reveals the focus distance of the eye. Using the projection of multiple patterns, various embodiments of the invention are given below, all based on the projection of multiple patterns each of which is focused at another distance. As long as the patterns are within the depth of field of the camera, the detection of a particular pattern reveals the focus at the associated distance.

The camera CAM has an image sensor IS. The signals of the image sensor IS are sent to an image processing unit IP to measure the sharpness of the image.

Figure 5A:
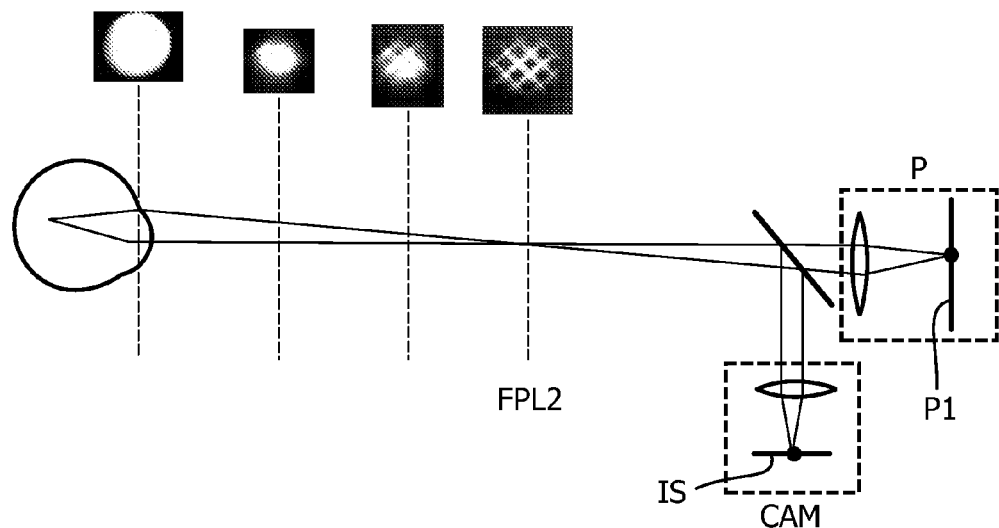
FIGS. 5A, 5B and 5C show possible set-ups for a device and method in accordance with the invention.
Figure 5B:
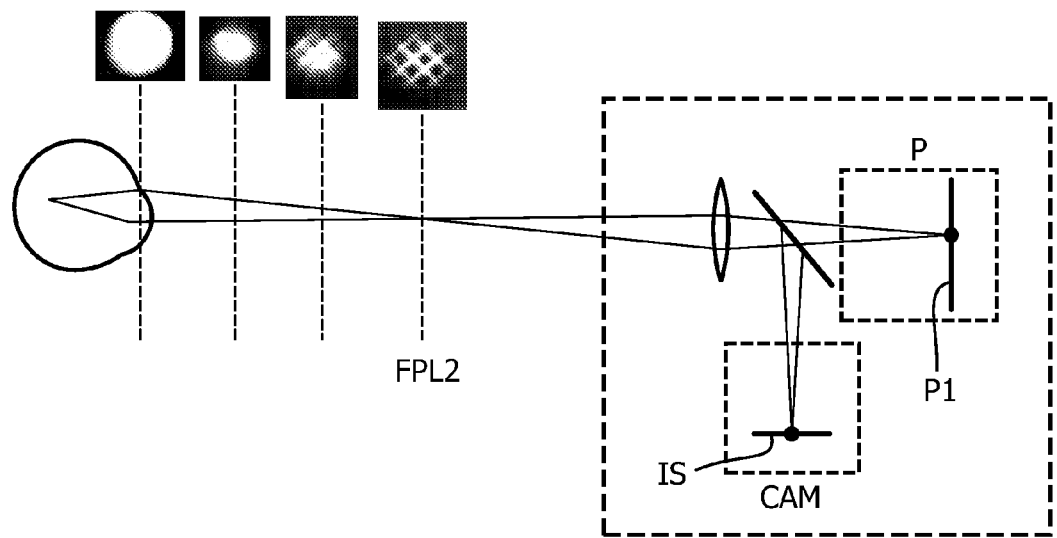
Figure 5C:
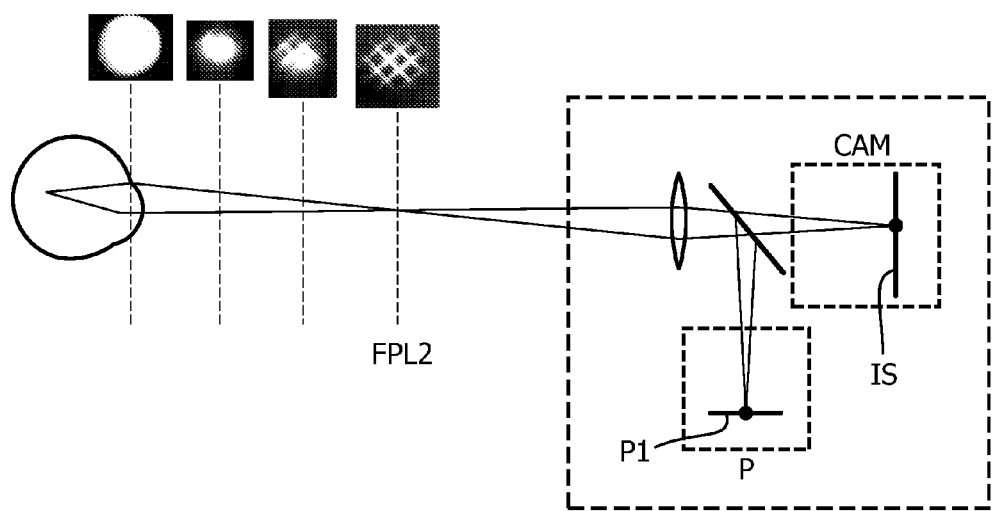

FIGS. 5A, 5B and 5C show possible set-ups for a device in accordance with the invention.

In FIG. 5A the projector and the camera each have a separate lens, in FIG. 5B the projector and the camera share a common lens. This reduces the number of elements of the system. In FIG. 5C the position of camera and projector has traded places compared to FIG. 5B. This is a preferred embodiment. It is better to have the camera look straight through the beam splitter. Of course, in FIG. 5A camera and projector can also trade places.

FIGS. 5A to 5C also show the images taken by the camera of the pattern reflected at the retina of an eye. When the focal plane of the eye FLP2 coincides with the focal plane of the projector and camera a relatively sharp image is seen, this image becomes progressively blurred as the focal plane of the eye differs from the focal plane of the projector and camera. The observed images where taken by the coaxial camera when changing its focus during steady state focus of the external imaging system (indicated in the drawing by the eye). Sweeping the focal plane of the projector and camera through a range and simultaneously recording the image and, using image processing, determining the sharpness of the image, provides a maximum of sharpness at a particular focal plane for the projector and camera. The focal plane of the eye corresponds to the so found focal plane.

The pattern may be provided in infrared (IR) light.

The pattern may also, in preferred embodiments, be provided in each alternate video frame, such that the camera alternately acquires a background image and an image with the projection of the luminous patterns. Subtraction of the background image leaves only the reflection of the luminous pattern on the retina, thereby significantly enhancing the detectability of the reflection of the pattern.

The pattern may also, in preferred embodiments be given a temporal frequency, e.g. 70 Hz. Preferably the frequency does not correspond to for instance frequency used other sources of visible or infrared light. The camera may then be tuned to that frequency by using a frequency filter to filter out IR signals that are not in a range of frequencies around the frequency of the projector. In such preferred embodiments back ground signals are filtered out.

Figure 6:
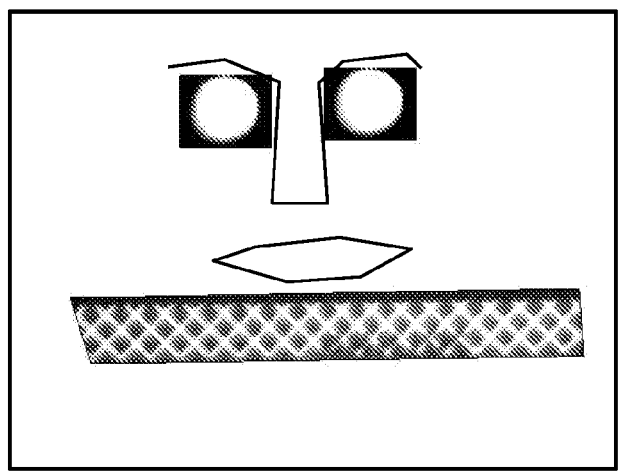
FIG. 6 illustrates the reflection of a pattern on the retina, as captured on the image sensor of a camera, when the pattern is swept through a range.
Figure 6:
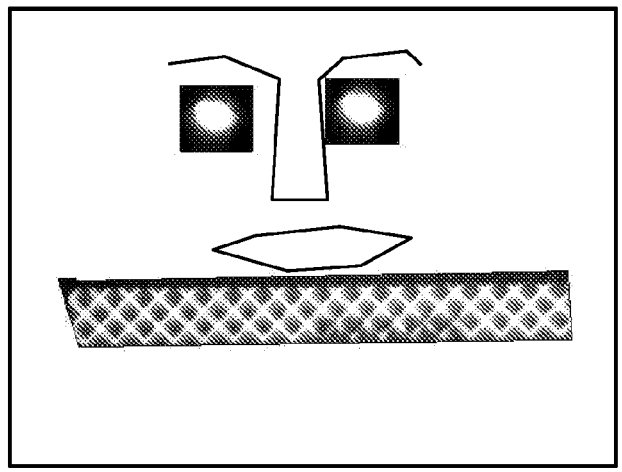
Figure 6:
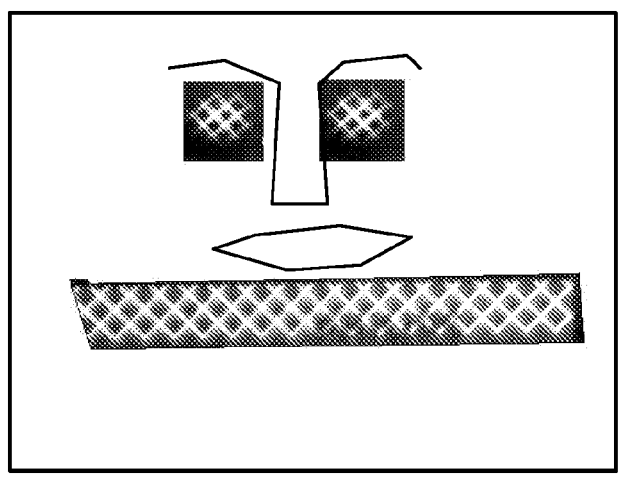

FIG. 6 illustrates the reflection of a pattern on the retina, as captured on the image sensor of a camera, when the pattern is swept through a range.

Figure 7A:
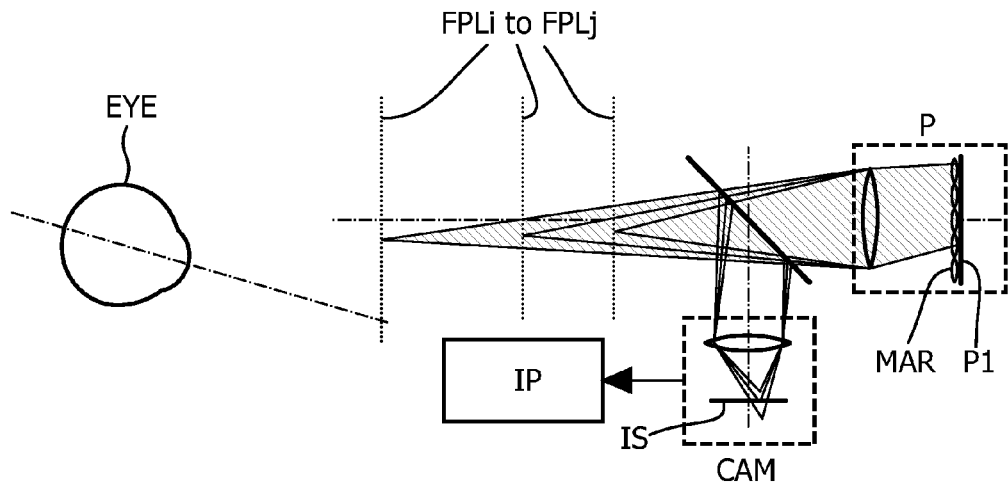
FIG. 7A to 7C illustrate embodiments of a system according to the invention.
Figure 7B:
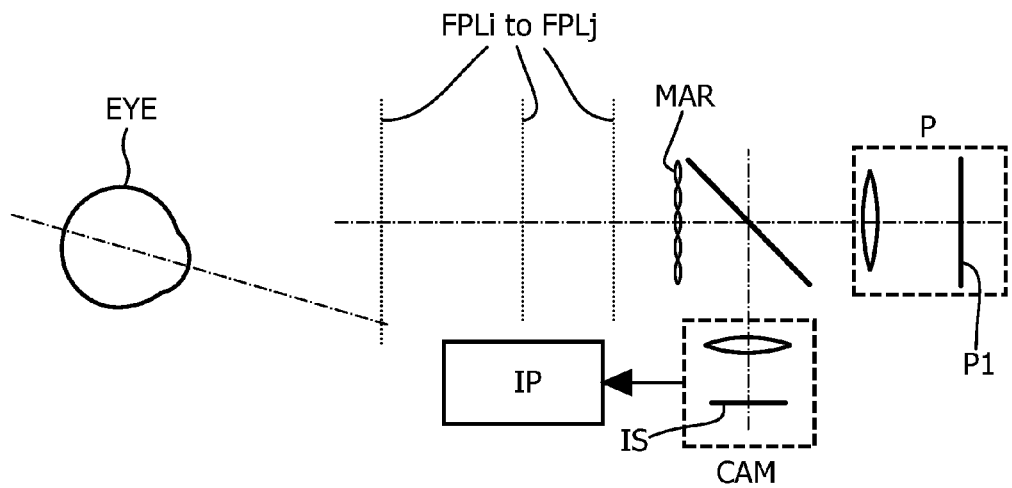
Figure 7C:
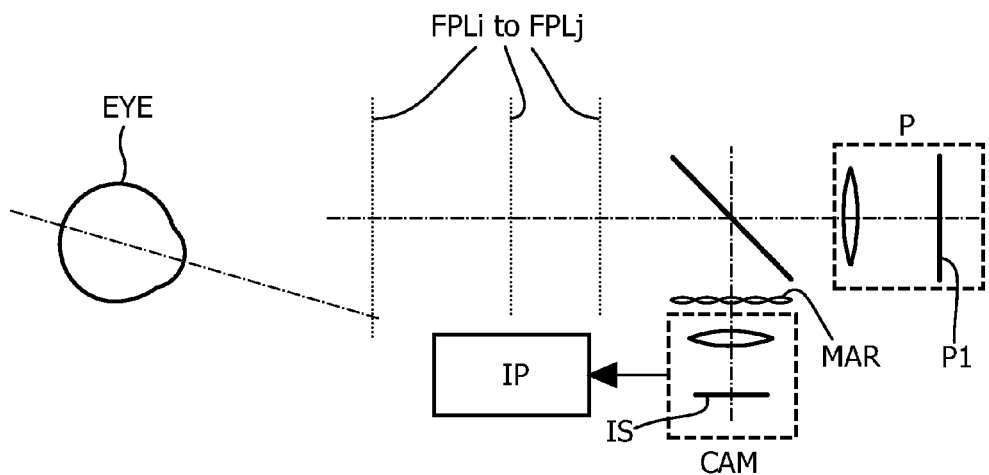

FIGS. 7A to 7C illustrate an embodiment of a system and method of the invention. The difference between this embodiment and the previous embodiment is that multiple focal planes FPLi to FPLj are made using a microlens array. The system of these embodiments comprises a microlens array MAR placed in the path of the projector to create light field that contains different patterns each of which focused at a different distance. Using this technique, it is possible to create either a stack of discretely focused patterns, or a continuous pattern of which a known aspect varies as function of distance. Such a pattern can be a grating pattern; the orientation of the pattern can then be used as a known aspect of the pattern. By analyzing the image on the camera one can find the focal plane of the eye. The simultaneous projection at different distances also allows the estimation of individual ocular accommodation among multiple subjects within the range of the system. This is impossible with known systems. In FIG. 7A the microlens array is positioned in the projector light path, similar effects are obtained by placing the microlens array in the light path of the camera, in which case instead of a plenoptic projector a plenoptic camera is used. This arrangement is shown schematically in FIG. 7C. In preferred embodiments the micro lens array is positioned in front of both the camera and the projector, as schematically shown in FIG. 7B. The latter arrangement provides for a 1:1 relation ship between projector and camera pixels which is advantageous.

Instead of a microlens array the projector can contain a stack of different slides at different distances behind the projector lens, each of which having a different pattern.

The pattern mask can also be a diffractive element generating a light-field with different characteristics at different distances. A hologram may be used for this purpose.

The generation of a pattern (or patterns) at multiple distances can also be performed in a time sequential fashion, provided that the camera uses synchronized image capture.

It is also possible to use more than one projector projecting static patterns at different distances, using mirrors to bring the optical axes of the projectors in line with each other.

Given the suitable pattern, the blur of the pattern can instantly identify the direction in which its projection is out of focus. This can be used to mechanically control the focus of the projector (and the camera) to keep the relayed pattern in focus. The control system then automatically reveals the focus distance of the unknown system, i.e. the focal plane of the eye. Disadvantage is that it can adjust to one single unknown camera or single human subject; this, in contrast to the use of simultaneous multiple-pattern projection. The system and method is described here for tracking accommodation of an eye, it is remarked that a camera functions in similar fashion as an eye and the system can thus also be used to track the focus of a camera.

Figure 8:
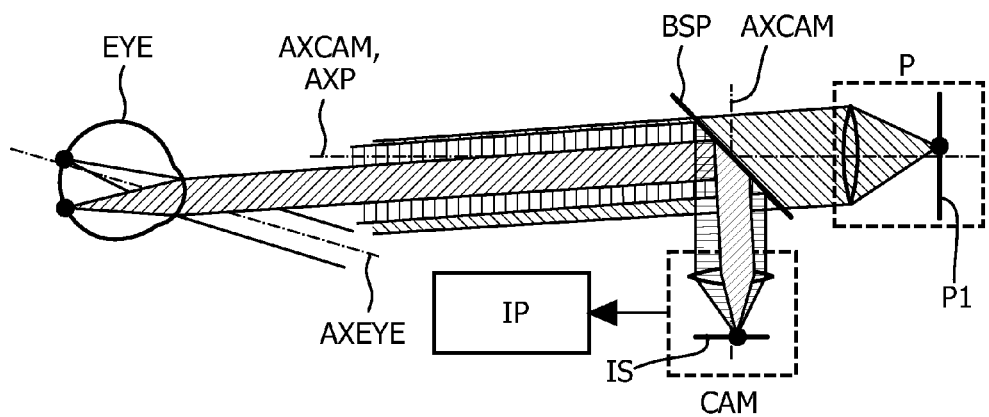
FIG. 8 illustrates that the system may be used to distinguish whether an eye is focused on infinity.

The system is also capable of detecting when an eye is focusing at infinity. Even though the focal plane of the projector and the focal plane of the eye cannot coincide in such circumstances, nevertheless, the pattern on the sensor of the camera will be sharply imaged when the eye is focusing at infinity. FIG. 8 illustrates such a situation. The parallel light rays emitted by the projector are focused by the eye, when focusing on infinity, on the retina and the light rays reflected from the retina form parallel rays, these are focused on the sensor of the camera. Thus the system is able to establish whether or not the eye is focusing on infinity.

In the circumstances where patterns are formed at various focal planes one pattern may be reserved for infinity. Methods for measurement of sharpness are known. One way of measuring sharpness is for instance to measure the extent of lines in the pattern, and/or the ratio between maxima and minima in the reflected pattern. The extent of lines in the pattern will be show a minimum and the ratio a maximum, when the pattern is focused, i.e. sharp.

Figure 9:
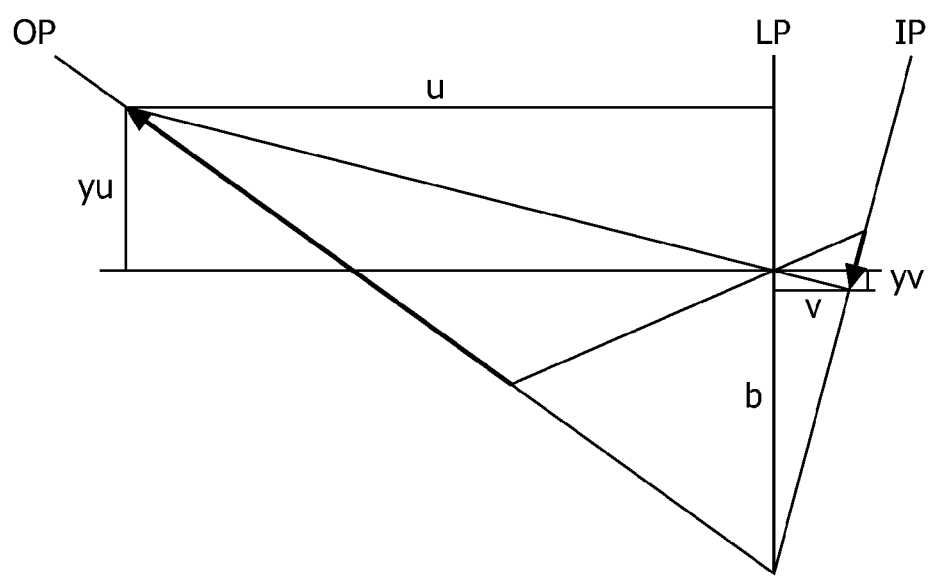
FIG. 9 illustrates rotation of the focal planes

Furthermore, as mentioned earlier, the volume of coincident focus decreases when the angle between the two optical axes, optical axis of the eye and the optical axis of the projector and camera becomes larger. We can compensate for this rotation by rotating the focus plane of the projector and, if necessary, of the camera. FIG. 9 illustrates the rotation of the focus plane of the projector. This is achieved by rotation of the image plane with respect to the lens plane, know as a Scheimpflug configuration, first proposed by Theodor Scheimpflug, see for instance GB patent no. 1196, May 1904. This tilted lens geometry, named after its inventor, cases the focus plane to acquire a rotation with respect to the lens plane. The extended focus plane will intersect the extended lens plane as well as the extended image plane at the same line. Alternatively, one can use several pairs of a projector and a camera looking at the to be observed eye and analyzing the various reflected patterns.

Figure 10:
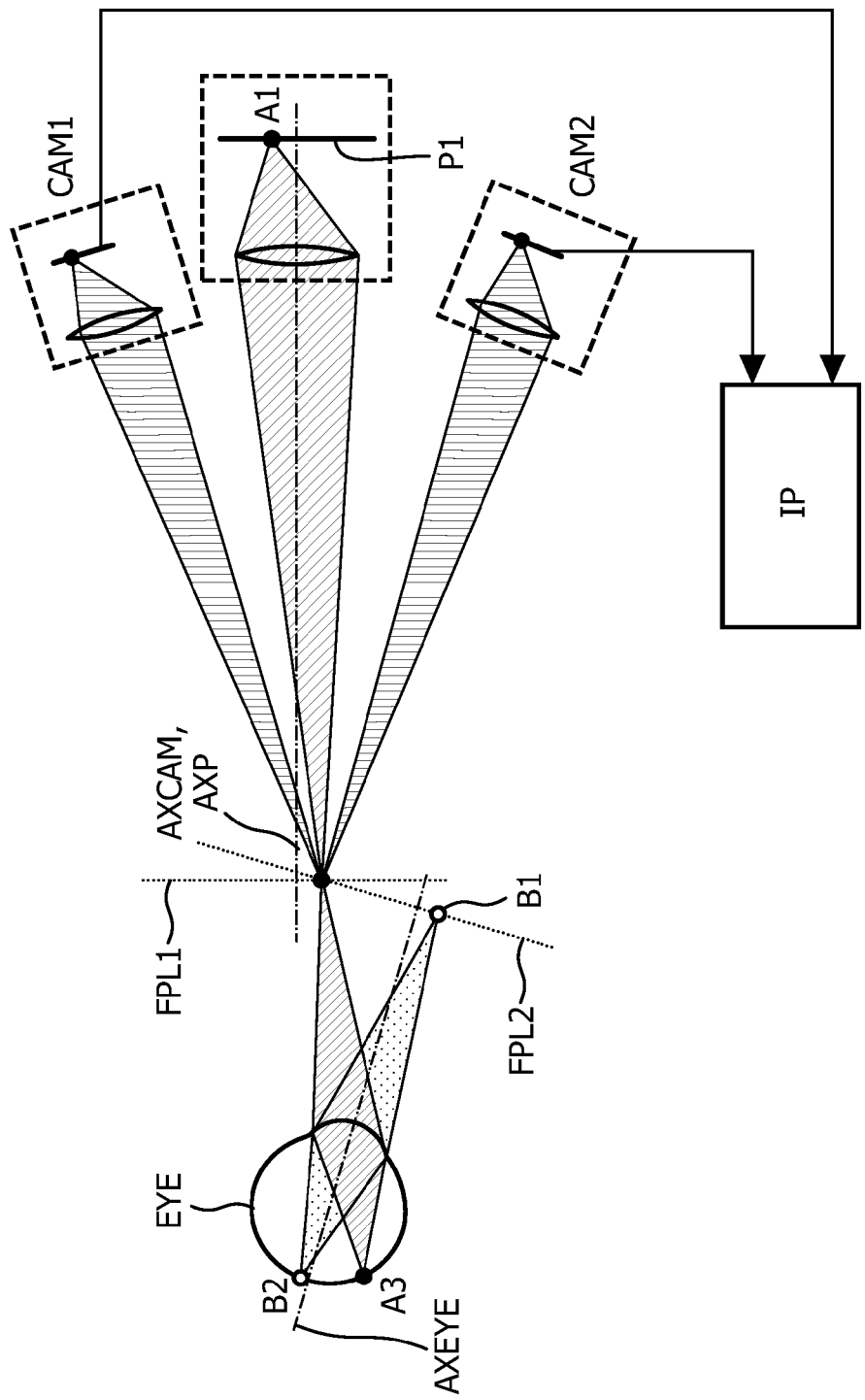
FIG. 10 illustrates a further embodiment of a system and method of the invention.

In the example of the method of the invention of FIG. 10 the projector is surrounded by an array of camera, Cam 1, cam 2 etc wherein in this example the projector. Using an area of cameras one can establish a light field, at the centre of the array. Using the images provided by the array of cameras images at various depth of field can be reconstructed. This allows depth information to be obtained from the images taken by the array of cameras. The advantage of this method is that no depth information has to be known in advance. The position of the eye can be obtained by analyzing the images of the array of cameras.

The system and method in all embodiments can be used to track vital signs:

When humans continue to focus on a fixed distance, this steady-state ocular accommodation is known to vary with the periodic respiration as well as with the heartbeat. As such, the detection of accommodation can also provide these vital signs. The fact that the system of the invention can do this in an unobtrusive manner and from a distance offers possibilities not yet possible. For instance when the heart rate and periodic respiration of a person who is undergoing an endurance test is to be measured this can be done without having to bother the person with wires.

On the other hand, given externally measured vital signals, the measurement of ocular accommodation can in principle be corrected for the modulation they induce on the focusing distance.

The camera used may be a light field camera, i.e. a camera that is able to provide image data that can be used to make an image that in is focus at a range of field depth. There are various methods to convert a conventional camera into a light-field camera with a synthetic aperture. The advantage of a light-field camera is that, in a single exposure, it integrally captures a complete filed of light rays, from which it is possible to retrospectively adjust focus or focus range on the basis of a single captured frame. As such, a captured light-field instantly provides an estimate or measurement of the focus distance of the remote eye or eyes. Such a camera can be constructed using a microlens array in front of the sensor, by the use of a coded aperture or a modulating pattern in the optical path between lens and sensor (dappled photography).

Various methods exist to extend the depth of field of a camera without sacrificing the exposure. These methods are particularly interesting in when the camera is only used for the detection of particular patterns and not for the capture of regular image capture. A known method is the use of a focal sweep imaging.

In embodiments of the invention focus detection is used in combination with gaze detection.

By combining gaze detection and focus detection it becomes possible to disambiguate unintentionally staring from intentionally gazing in the direction of a device. In this case the system is part of a particular device that is to be controlled on the basis of gaze, possibly in combination with another trigger coming from a button or from the interpretation of a spoken command.

Particularly by choosing the projected focal plane to be positioned at the device itself, it is possible to detect intentional focus in addition to gaze. In case of detected gaze without detecting proper focus can be regarded as unintentionally staring and disregarded as a trigger to start controlling the device.

As gaze detection is already based on the use of a camera and coaxial (infrared) illumination, gaze detection and focus detection can be efficiently integrated at little extra cost.

Use of focus detection or estimation in combination with gaze estimation.

The combination of gaze estimation allows the detection of a point of gaze in 3D space. A combination with a (holographic) 3D display may enable unique functionalities.

The system and method of the invention may be used for or in several applications.

Remote estimation of ocular accommodation in humans can be used for sensing attention, for measuring the visual attention with the context of digital signage, possibly in combination with gaze detection. Knowledge with regard to the focusing distance can help to disambiguate 'seeing' and 'staring'.

Also possibly in combination with gaze detection, it can be used as an attentive user interface that only responds to a spoken command or to a gesture when it is being looked at.

The remote measurement of ocular accommodation can also be used in the detection of visual defects in children to monitor the correct development of the visual system.

The detection of accommodation at infinity can reveal if a driver exhibits sufficient focus on the road.

As part of a gaze controlled user interface for disabled people, it may provide robustness, e.g., in mouse control.

Combined with an optical system it may provide a way to automatically adapt an optical system to the refractive condition of the eye. As the method works unobtrusively and allows a small form factor, the application may go beyond traditional ophthalmology and be part of an optical product for the consumer market.

In security systems, detection of human visual focus may be used to detect unwanted attention. Detection of unwanted camera focus can also be detected. As said, the system can also be use to measure the focal distance of a camera.

The unobtrusive nature makes the principle particularly suitable for applications with non-cooperating subjects, e.g. young children but also (wild) animals.

The invention also relates a computer programs comprising program code means for performing a method of the invention, in whatever embodiment, when said program is run on a computer. The invention also relates to computer program products comprising program code means stored on a computer readable medium for performing a method of the invention.

A camera is any device for recording images.

It could be a part of a device also used for other purposes such as communication, or attached to, integrated in or cooperating with such a communication device.

Yet a further embodiment lies in the use of luminous patterns in different wavelengths, for instance for instance three different wavelengths, one at either end of the visible range and at a center part of the visible range, for instance red-green-blue. Measuring the focal distances at three wavelengths provides information on the abberation of an eye. For each wavelength the focal distance can be measured, and this can be done simultaneously. This gives an instant and remote measurement not just of the ocular acccommodation, but also for the ocular accomodation in three different wavelengths, i.e. the abberation.

Also use can be made of hidden luminous patterns, i.e. patterns that are nearly invisible to the human eye. One way is using IR light for the luminous patterns.

Another way is to embed, in a manner that the human eye cannot see, a pattern in an it itself for the human eye non-distracting projected image.

A projector can project a simple white light area plus a pattern in one frame and a white light area minus said pattern in the next frame.

In one frame the projector projects white light (of less than maximum intensity) plus a pattern, in the next frame the projector projects white light minus the pattern. If the frame frequency is above the frequency perceivable for the human eye, the human eye will not perceive the pattern, but simply a white light lamp, because the human will average out the difference between the two projections leaving only a simple white area seen by the observer. White light lamps do not draw the attention of a viewer and therefore do not disturb the measurement. However, by subtracting two images taken by the camera for two frames, the reflection of the embedded luminous pattern is perceivable in the image recorded by the camera. The hidden, to the human eye that is, patterns in the projector may be different for different colors, which could also be used to hide the patterns even more. The sequence can be for instance:

I. White minus blue pattern plus green pattern, (in different structural patterns)
 II. White minus green pattern plus red pattern
 III. White plus blue pattern minus red pattern.

The patterns themselves need not be the same, but may differ.

The eye will, if the frame frequency is above approximately 50 Hz, perceive a white lamp. The camera, however, can, by subtracting II from I and taking the 'green signal', extract the reflection of the green pattern. Likewise, it can extract the reflection, by appropriate subtracting of frames, of the blue and red pattern.

Another way of making the patterns invisible is for instance by using a checkerboard pattern in two colors (e.g. A-B) the summation of which is white to the human eye. In one frame the checkerboard pattern is A-B, in the next frame B-A. Again, the human eye will perceive a white light which does not show a pattern, but the camera can, by appropriate subtraction or measurement of frames, extract the reflection of the A and B patterns.

Yet another way is to use a pattern that comprises three or more differently colored parts (for instance a honeycomb pattern with colors A-B-C). By using a repeating cycle of three of more frames (A-B-C; C-A-B; B-C-A; A-B-C etc) wherein as an average over a cycle at all parts the human eye sees white light any underlying pattern is invisible to the human eye.

However, the signals of the recording camera can be analysed to extract information on the reflected patterns in the three or more colors. The number of colors can be extended to four or more to extract more detailed information on abberations.

The method can be used to provide information on for instance the operation of the humane eye in various ways. For instance: by measuring the reaction of an eye or two eyes of a viewer wherein the eyes follow an object that is moved within the filed of view of the viewer it is possible to get information on:

The range of distances at which the eye or eye can focus.

In most circumstances one can simply ask a person for this information. However, there are also circumstances in which this is not possible because the person cannot communicate and/or a person simply cannot stand the tests required in normal procedures for reasons of physical or mental health. Even simply providing a reasonable estimate for parameters of the eye will result in significant advantages since the time and effort to get good results for any test (and thus the time a patient must undergo the test) is amongst others determined by the starting point for the tests. Therefore, providing a good starting point for more accurate measurements in an unobtrusive manner can greatly benefit a patient.

By measuring for both eyes differences between the eyes can be detected and measured, which can give an indication of the amount of anisometry. The invention can for instance be used to provide indications of amblyopia at an early age by detecting differences between eyes while a child is e.g. playing with a toy or looking at a moving object.

Means for performing a step in the method can be in the form of hardware, software or any combination thereof. In the systems and devices according to the various embodiments of the inventions means are provided for performing the steps of the method. Where in the description or claims "means for" are mentioned followed by more than one of the methods step, the means can be a combined means for performing all of the steps, or a short hand notation for a number of means, each of said means for performing one or more of the steps of the method. So, 'means for generating' can be called a generator for generating, The various means have been described as separate for the ease of description. This does not mean that the invention would be restricted to such means being separate units, functions could be combined in an integrated device or piece of software.

In short the invention can be summarized as follows:

A system and method measures an optical focus of a distant optical imaging system, in particular the ocular accommodation of a distant human subject. A luminous pattern of light is projected in focus at a known focal plane in front of the distant optical imaging system, and an image of the reflection of the pattern on a sensor surface of the distant optical imaging system, for instance the retina of an eye, is recorded by a camera having an optical axis coinciding at least partly with or situated close to the optical axis of the projection device. The sharpness of the luminous pattern reflected on the sensor surface is determined.

The invention claimed is:

1. A measurement system for remote measurement of an optical focus of a distant optical imaging system, the distant optical imaging system comprising a lens and a sensor surface, wherein the measurement system comprises:
    a light projection device (P) for projecting a luminous pattern of light such that the pattern is in focus at a known focal plane (FPL1) in front of the lens of the distant optical imaging system;
    a camera (CAM) having an optical axis (AXCAM) which, between the light projection device (P) and the known focal plane (FPL1), at least partly coincides with the optical axis (AXP) of the light projection device (P), for recording an image of the reflection of the luminous pattern on the sensor surface of the distant optical imaging system: and
    an image processing unit (IP) for determining a sharpness of the recorded luminous pattern reflected on the sensor surface for measuring a focal distance of the distant optical imaging system.

2. The system as claimed in claim 1, wherein the light projection device (P) is arranged to simultaneously generate more than one luminous pattern at different focal planes or a continuous luminous pattern of which a known aspect varies as a function of the position of the focal plane.

3. The system as claimed in claim 2, wherein the light projection device (P) comprises a microlens array (MAR) for creating a light field comprising the more than one luminous pattern at different focal planes or the continuous luminous pattern of which a known aspect varies as function of the position of the focal plane.

4. The system as claimed in claim 2, wherein the light projection device (P) comprises a stack of different slides at different distance behind a projector lens for simultaneously creating the more than one luminous pattern at different focal planes.

5. The system as claimed in claim 2, wherein the light projection device (P) comprises a diffractive element generating a light-field with different characteristics at different distances for simultaneously generating more than one luminous pattern at different focal planes or a continuous luminous pattern of which a known aspect varies as function of the position of the focal plane.

6. The system as claimed in claim 5, wherein the system comprises a common microlens array positioned in front of both the camera (CAM) and the light projection device (P).

7. The system as claimed in claim 2, wherein the camera (CAM) is a light-field camera.

8. The system as claimed in claim 1, wherein the light projection device (P) projects IR light.

9. The system as claimed in claim 1, wherein the light projection device (P) is arranged to project more than one luminous pattern with a temporal frequency, and wherein each luminous pattern has a distinctive temporal frequency.

10. The system as claimed in claim 1, wherein the light projection device (P) is arranged to project patterns in different wavelengths.

11. The system as claimed in claim 1, wherein the projection device (P) projects the luminous pattern or patterns in a wavelength invisible to a human eye.

12. A method for remotely measuring an optical focus of a distant optical imaging system, the distant optical imaging system comprising a lens and a sensor surface, the method comprising the steps of:
    projecting a luminous pattern of light in focus at a known focal plane in front of the lens of the distant optical imaging system by a light projection device;
    recording an image of the reflection of the luminous pattern on the sensor surface of the distant optical imaging system by a camera having an optical axis which, between the light projection device and the known focal plane, at least partly coincides with the optical axis of the projection device; and
    analyzing sharpness of the recorded luminous pattern reflected on the sensor surface for measuring a focal distance of the distant optical imaging system.

13. The method as claimed in claim 12, wherein more than one luminous pattern is simultaneously projected at different focal planes or a continuous luminous pattern of which a known aspect varies as a function of the position of the focal is projected.

14. The method as claimed in claim 12, wherein IR light patterns are projected.

15. The method as claimed in claim 12, wherein more than one luminous pattern is projected and each luminous pattern is projected with a distinctive temporal frequency.

16. The method as claimed claim 12, wherein luminous patterns in different wavelengths are projected.

17. The method as claimed in claim 12, wherein ocular accommodation is measured, the distant optical system is an eye, and the sensor surface is the retina of the eye.

18. Computer program product comprising program code means stored on a non-transitory computer readable medium for performing a method according to claim 12 when said program is run on a computer.

* * * * *